(12) United States Patent
Lasso et al.

(10) Patent No.: US 11,285,073 B2
(45) Date of Patent: Mar. 29, 2022

(54) APPARATUS FOR APPLYING PERIODIC PRESSURE TO THE LIMB OF A PATIENT AND METHOD OF USE

(71) Applicants: John Nigel Lasso, Laguna Hills, CA (US); Trevor James Theriot, Newport Beach, CA (US)

(72) Inventors: John Nigel Lasso, Laguna Hills, CA (US); Trevor James Theriot, Newport Beach, CA (US)

( * ) Notice: Subject to any disclaimer, the term of this patent is extended or adjusted under 35 U.S.C. 154(b) by 640 days.

(21) Appl. No.: 16/167,505

(22) Filed: Oct. 22, 2018

(65) Prior Publication Data

US 2020/0121546 A1 Apr. 23, 2020

(51) Int. Cl.
*A61H 9/00* (2006.01)
*A61B 17/135* (2006.01)

(52) U.S. Cl.
CPC ........ *A61H 9/0092* (2013.01); *A61B 17/1355* (2013.01); *A61H 9/0085* (2013.01); *A61H 2201/5035* (2013.01); *A61H 2201/5074* (2013.01); *A61H 2205/10* (2013.01)

(58) Field of Classification Search
CPC ............... A61H 9/0092; A61H 9/0085; A61H 2205/10; A61H 2201/5074; A61H 2201/1409; A61H 2201/5097; A61H 2201/165; A61H 2201/0157; A61H 2201/1207; A61H 2209/00; A61H 2201/0103; A61H 2201/5007; A61H 2201/1642; A61H 1/00; A61H 9/0078; A61H 2201/5035; A61B 17/1355
See application file for complete search history.

(56) References Cited

U.S. PATENT DOCUMENTS

| | | | |
|---|---|---|---|
| 10,166,166 B1* | 1/2019 | Theriot | A61H 9/0092 |
| 2004/0260218 A1* | 12/2004 | Shah | A61H 31/00 |
| | | | 601/152 |
| 2005/0043655 A1* | 2/2005 | Schenck | A61N 1/321 |
| | | | 601/15 |
| 2010/0324429 A1* | 12/2010 | Leschinsky | A61B 17/135 |
| | | | 600/493 |
| 2014/0194796 A1* | 7/2014 | Noskowicz | A61H 9/0092 |
| | | | 601/151 |
| 2014/0303533 A1* | 10/2014 | Zeutzius | A61H 9/0092 |
| | | | 601/151 |

(Continued)

*Primary Examiner* — Quang D Thanh
(74) *Attorney, Agent, or Firm* — Ruben Alcoba, Esq.

(57) ABSTRACT

An apparatus for applying periodic pressure to the limb of a patient to prevent deep vein thrombosis and pulmonary embolism. The apparatus has a cuff that has a bladder. A housing that is attached to the cuff. A pump for inflating the bladder to a maximum cuff pressure, the maximum cuff pressure being 55 mmHg, and the pump is housed within the housing. A plurality of pressure application modes each of which control operation of the pump and wherein each pressure application mode is progressively applied in a manner that will increase a patient's blood flow. A pressure application mode selector is disposed on the housing. A microprocessor that is equipped with a program that controls the pump and the plurality of pressure application modes. The microprocessor is housed within the housing and it is connected to a transceiver. And, a remote that connects to the transceiver.

2 Claims, 11 Drawing Sheets

(56) References Cited

U.S. PATENT DOCUMENTS

| | | | |
|---|---|---|---|
| 2015/0366565 A1* | 12/2015 | Shaltis | A61B 17/1355 606/202 |
| 2016/0022269 A1* | 1/2016 | Ganske | A61B 17/1355 606/202 |
| 2018/0098707 A1* | 4/2018 | Salamon | A61B 5/02416 |
| 2020/0268592 A1* | 8/2020 | Johnson | A61H 11/00 |

* cited by examiner

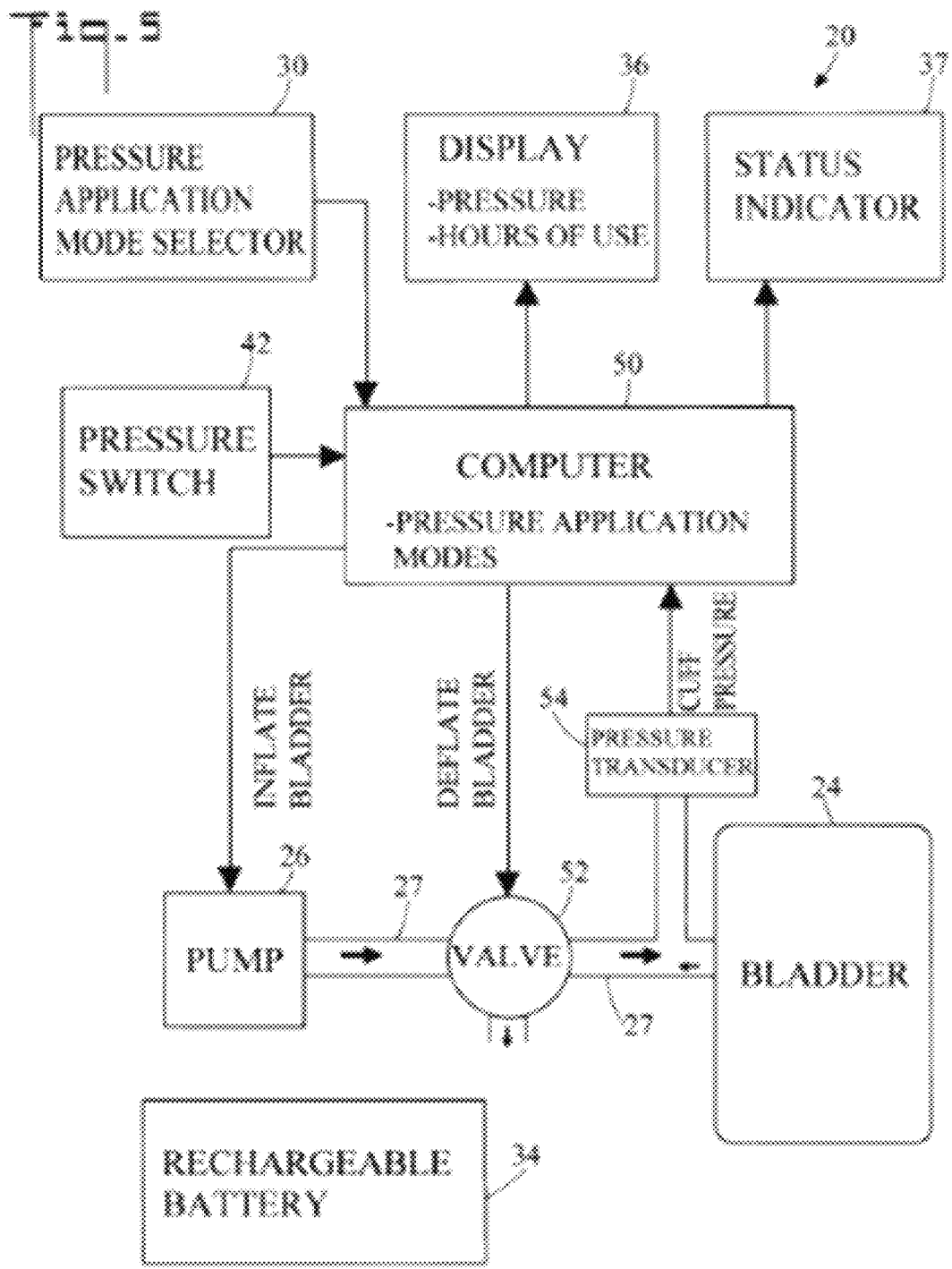

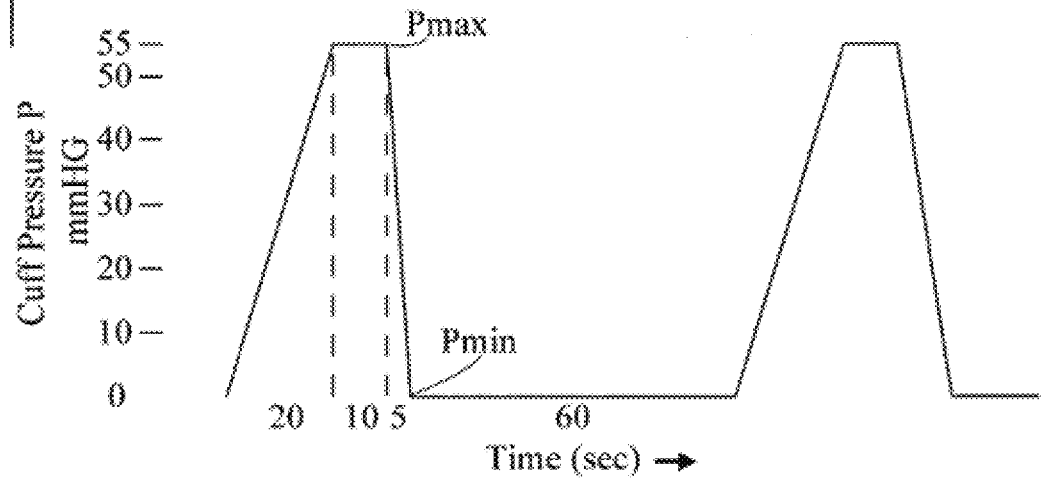
PRESSURE APPLICATION MODE 1
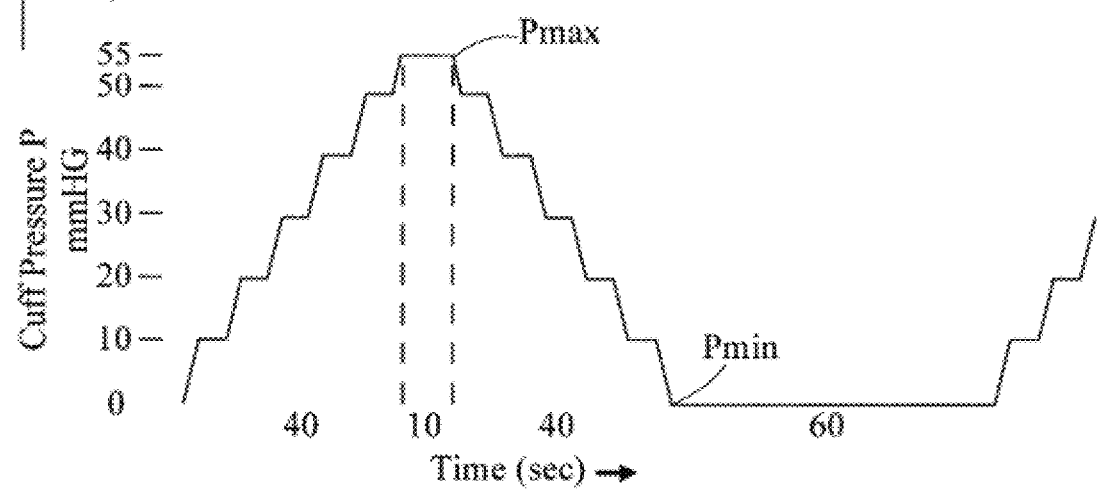
PRESSURE APPLICATION MODE 2

PRESSURE APPLICATION MODE 3

PRESSURE APPLICATION MODE 4

APPARATUS FOR APPLYING PERIODIC PRESSURE TO THE LIMB OF A PATIENT AND METHOD OF USE

CROSS REFERENCE TO RELATED APPLICATION

This application is a continuation in part of U.S. patent application Ser. No. 14/822,978, filed on Aug. 11, 2015 and being titled APPARATUS FOR APPLYING PERIODIC PRESSURE TO THE LIMB OF A PATIENT AND METHOD OF USE.

TECHNICAL FIELD

The present invention pertains generally to the field of medicine, and more particularly to an apparatus and method for preventing deep vein thrombosis and providing other medical benefits through the application of periodic pressure to the limb of a patient.

BACKGROUND OF THE INVENTION

Deep vein thrombosis (DVT) is a medical condition in which blood clots form within a deep vein. This occurs most frequently in the legs but can also occur in the arms and other parts of the body. If a formed clot detaches and travels to the lungs, severe complications and even death can occur. In the case of the limbs, prevention options for at-risk patients include the application of periodic compression pressure to the limb using an inflatable cuff. Pressure is alternately applied and then relaxed in a cyclic manner. This stimulates blood flow and reduces the risk of clot formation.

BRIEF SUMMARY OF THE INVENTION

The present invention is directed to apparatus for applying periodic pressure to a limb of a patient. That is, pressure is alternately applied and removed. The apparatus has numerous medical uses such as:
- Preventing deep vein thrombosis (DVT) such as in patients who will be stationary for long periods of time
- Enhancing blood circulation
- Diminishing post-operative pain and swelling
- Reducing wound healing time
- Treatment and assistance in healing: stasis dermatitis; venous stasis ulcers; arterial and diabetic leg ulcers
- Treatment of chronic venous insufficiency
- Reducing edema The apparatus comprises a cuff which is wrapped around the limb of the patient. The apparatus employs cyclic, periodic, pneumatic pressure (inflation followed by deflation) to compress the limb and stimulate the flow of blood. The apparatus is a portable unit in which the patient can select a particular pressure application mode from several available pressure application modes. The selected pressure application mode then determines how pressure is applied to the limb of the patient as a function of time. The selection is accomplished at the cuff which is wrapped around the patient's limb. The apparatus is intended to be used in the home, in travel situations where altitude or lack of mobility occurs, or in a clinical setting by or under the direction of a medical professional. The apparatus is a lightweight, rechargeable battery-powered, electromechanical control unit which provides and digitally monitors through two LED screens the inflation cycle for enhanced circulation therapy. All pump control components are protectively enclosed in a plastic casing which is attached to a cuff.

In accordance with an embodiment, apparatus for applying periodic pressure to the limb of a patient includes a cuff which has a bladder, the cuff is shaped and dimensioned to wrap around the limb of the patient. A pump inflates the bladder to a cuff pressure. A plurality of pressure application modes are available each of which can control the operation of the pump. A pressure application mode selector is disposed at the cuff. The pressure application mode selector allows a particular pressure application mode to be selected from the plurality of pressure application modes.

In another embodiment, the pressure application mode selector is operable by the patient.

In another embodiment, at least one of the pressure application modes of the plurality of pressure application modes has a maximum cuff pressure of 55 mmHg.

In another embodiment, at least one of the pressure application modes of the plurality of pressure application modes has a cycle which is repeated at least twice per minute.

In another embodiment, each pressure application mode of the plurality of pressure application modes has a minimum cuff pressure and a maximum cuff pressure. At least one of the pressure application modes of the plurality of pressure application modes is a step pressure application mode in which cuff pressure holds for a period of time at least one intermediate cuff pressure between the minimum cuff pressure and the maximum cuff pressure.

In another embodiment, the step pressure application mode contains a plurality of 10 mmHg steps.

In another embodiment, the minimum cuff pressure is 0 mmHg, the maximum cuff pressure is 55 mmHg, and the intermediate cuff pressures are 10 mmHg, 20 mmHg, 30 mmHg, 40 mmHg, and 50 mmHg.

In another embodiment, the pump is capable of raising the cuff pressure from 0 mmHg to 55 mmHg within two seconds.

In another embodiment, the pressure application mode selector is also a multi-purpose control which controls activation and deactivation of the apparatus.

In another embodiment, a display is disposed at the cuff. When the cuff is wrapped around the limb of the patient, the display is viewable by the patient.

In another embodiment, the display displays the cuff pressure.

In another embodiment, the display displays a cumulative number of hours of apparatus use.

In another embodiment, the cuff has an inside surface which when used abuts the limb of the patient. A pressure switch is disposed at the inside surface of the cuff, so that when the cuff is wrapped around the limb of the patient the pressure switch closes. If the pressure switch is not closed, the pump will not operate.

In another embodiment, the cuff includes a hook and loop fastener for securing the cuff to the limb of the patient. The hook and loop fastener includes an outwardly projecting tab which has a proximal end and a distal end. One of hook material and loop material is disposed at the distal end, and elastic material is disposed at the proximal end.

In another embodiment, a housing contains the pump. The housing is removably connected to the cuff by a plurality of screws.

Other embodiments, in addition to the embodiments enumerated above, will become apparent from the following detailed description, taken in conjunction with the accompanying drawings, which illustrate, by way of example, the principles of the apparatus and method of use.

BRIEF DESCRIPTION OF THE DRAWINGS

These and other features, aspects, and advantages of the present invention will become better understood with regards to the following description, appended claims, and drawings where:

FIG. 5 is a functional block diagram of the apparatus;

FIG. 6 is a first pressure application mode;

FIG. 7 is a second pressure application mode;

DETAILED DESCRIPTION OF THE INVENTION

Figure 1:
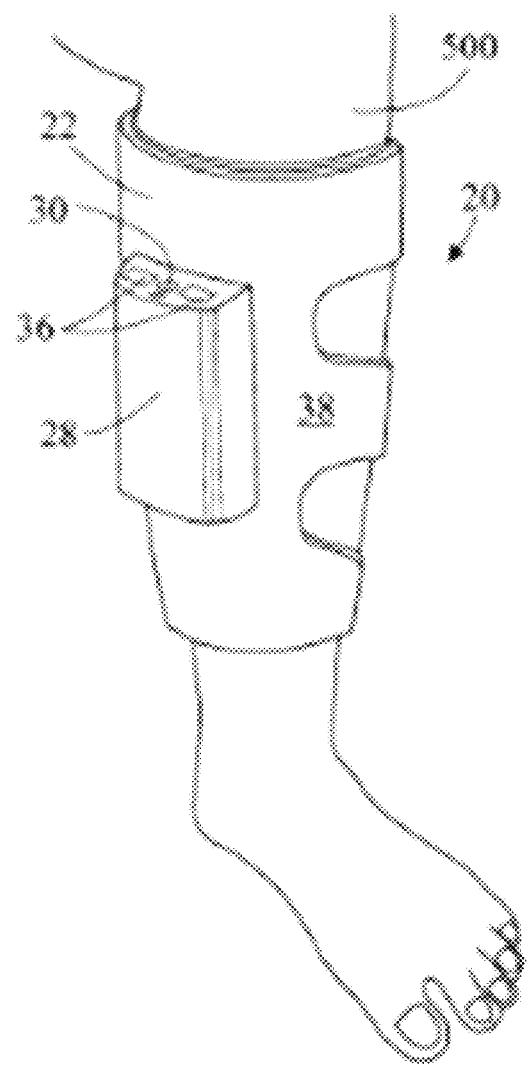
FIG. 1 is a perspective view of apparatus for applying periodic pressure to the limb of a patient.
Figure 2:
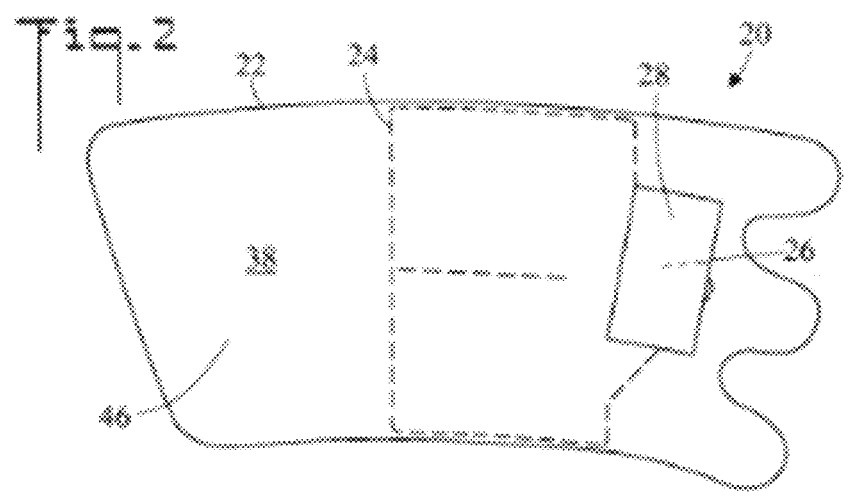
FIG. 2 is a top plan view of the apparatus.
Figure 3:
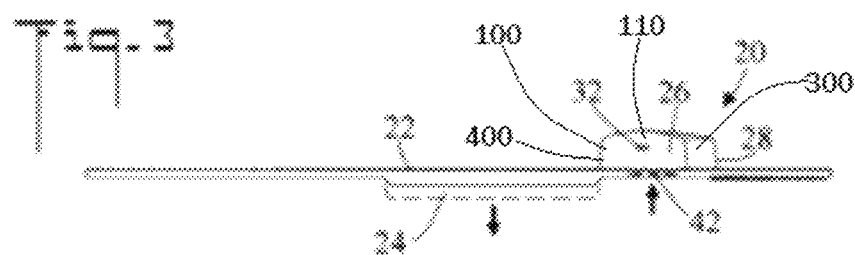
FIG. 3 is a side elevation view of the apparatus.
Figure 4:
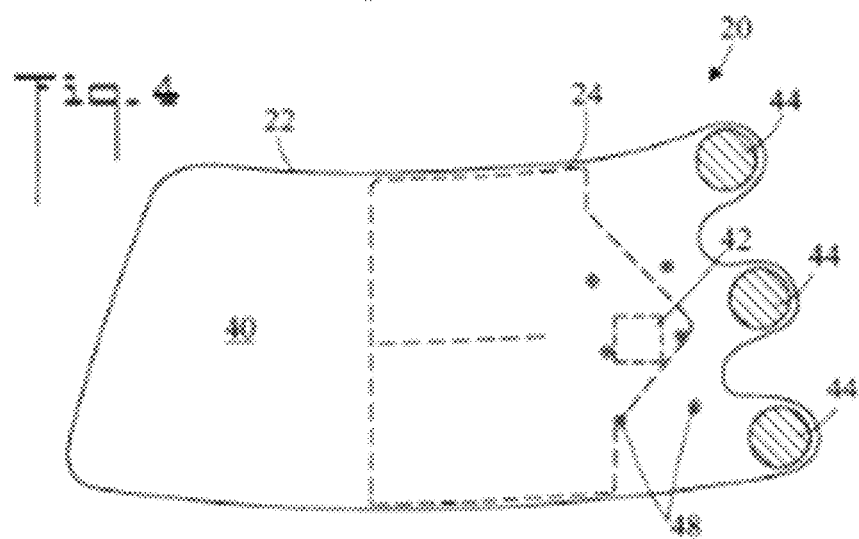
FIG. 4 is a bottom plan view of the apparatus.

Referring initially to FIG. 1, there is illustrated a perspective view of apparatus for applying periodic pressure to the limb 500 (as shown a calf) of a patient, the apparatus generally designated as 20. FIGS. 2-4 are top plan, side elevation, and bottom plan views respectively of apparatus 20, and FIG. 5 is a functional block diagram of apparatus 20. Apparatus 20 includes a cuff 22 which has an inflatable bladder 24, the outline of which is shown in broken lines in FIGS. 2 and 4. In the shown embodiment, bladder 24 has a single chamber. Cuff 22 is shaped and dimensioned to wrap around the limb 500 of the patient, much in the same manner as is a device for measuring blood pressure. Cuff 22 carries a pneumatic pump 26 for inflating bladder 24 to a cuff pressure P. That is, inflated bladder 24 causes cuff pressure P to be applied to the limb 500 of the patient. In the shown embodiment, pump 26 is located within a housing 28 which is removably connected to cuff 22 (refer also to FIG. 5 and the associated discussions). A plurality of different pressure application modes are available each of which can control the operation of pump 24 and cause cuff pressure P to assume a pre-programmed value as a function of time (refer also to FIGS. 6-9 and the associated discussions). A pressure application mode selector 30 is disposed at cuff 22. In the shown embodiment pressure application mode selector 30 is disposed on housing 28 which is connected to cuff 22. Pressure application mode selector 30 allows a particular pressure application mode (i.e. one of the pressure application modes) to be selected for use (by the patient) from the plurality of pressure application modes. That is, the patient can select the time dependent manner in which the pressure is applied to limb 500. In FIG. 3 the expansion of bladder 24 is shown in broken lines. Also, in FIG. 3 it is noted that housing 28 contains a charging port which is utilized to recharge a rechargeable battery 34 located within housing 28.

A display 36 is disposed at the cuff 22. In the shown embodiment, display 36 is disposed on housing 28. Referring specifically to FIG. 1, when cuff 22 is wrapped around the limb 500 of the patient, display 36 is viewable by the patient. That is, display 36 faces the head of the patient so that it can be readily seen. A status indicator 37 such as a light is also disposed at cuff 22.

Cuff 22 has an outside surface 38 upon which in the shown embodiment housing 28 is disposed, and an opposite inside surface 40 which when used abuts the limb 500 of the patient. A pressure switch 42 is disposed at inside surface 40 of cuff 22, so that when cuff 22 is wrapped around the limb 500 of the patient the pressure of wrapping causes pressure switch 42 to close. In the shown embodiment, pressure switch 42 is disposed just underneath inside surface 40 of cuff 22. If pressure switch 42 is not closed, pump 26 will not operate. In other words, cuff 22 must be securely wrapped around the limb 500 of the patient in order for the pressure switch 42 to close and the apparatus 20 to operate.

In the shown embodiment, cuff 22 includes a hook and loop fastener for securing cuff 22 to the limb 500 of the patient. Hook material 44 is disposed on inside surface 40 of cuff 22, and loop material 46 is disposed on outside surface 38.

In an embodiment, housing 28 is removably connected to cuff 22. The connection is effected by a plurality of screws 48 (six as shown). Referring to FIG. 5, in the shown embodiment the following components are located in or on housing 28; pump 26, conduit 27, pressure application mode selector 30, rechargeable battery 34, display 36, status indicator 37, valve 52, and pressure transducer 54. Housing 28 also contains a computer 50 which controls operation of apparatus 20, and a pneumatic valve 52 which is disposed between pump 26 and bladder 24.

Referring specifically to FIG. 5, there is shown one implementation of apparatus 20. Apparatus 20 includes a cuff 22 (refer to FIGS. 1-4) which carries the other apparatus components. Cuff 22 includes of a polyvinyl chloride (PVC) single chamber air bladder 24 which is encased inside a soft, non-woven medical fabric made from a polyester blended medical fabric or equivalent, which is adhered to the PVC air bladder 24.

Pneumatic pump 26 inflates bladder 24 via a conduit 27 (tube) in accordance with an inflate bladder signal received from computer 50. The inflation of bladder 24 is in accordance with one of a plurality of pressure application modes (refer to FIGS. 6-9 and the associated discussions) which are stored in the memory of computer 50. A valve 52 is disposed between pump 26 and bladder 24. During inflation valve 52 directs air from pump 26 to bladder 24 (large arrows). During bladder deflation, a deflate bladder signal causes valve 52 to vent the air in bladder 24 to the atmosphere (small arrows). A pressure transducer 54 communicates with conduit 27, measures cuff pressure P, and sends the current cuff pressure P to computer 50.

Computer 50 controls operation of apparatus 20, and includes a plurality of stored pressure application modes (M1, M2, M3, etc.) any of which can be selected by the patient. In an embodiment, computer 50 is a microcontroller 50.

A pressure switch 42 ensures that cuff 22 is securely wrapped around the limb 500 of the patient so that the application of pressure will be effective. The inflation process will not start unless the cuff pressure switch 42 is closed by proper snug wrapping.

Pressure application mode selector 30 is used by the patient to select the desired pressure application mode from the plurality of pressure application modes stored in computer 50. When apparatus 20 is turned on a default pressure application mode will be selected by computer 50 (e.g. pressure application mode M1). Then if the patient wants to change to a different pressure application mode, the pressure application mode selector 30 is simply pressed to move to the next pressure application mode. Pressure application mode selector 30 is a multi-function control and also serves to turn apparatus 20 on and off. Pressing pressure application mode selector 30 once initially turns the apparatus 20 on, and pressing and holding pressure application mode selector 30 for three seconds turns apparatus 20 off.

Display 36 includes two LED screens which display cuff pressure P, the selected pressure application mode M1, M2, M3, etc., and cumulative hours of apparatus 20 use. Display 36 is oriented so that it can be easily seen by the patient when apparatus 20 is wrapped around a limb and operating.

Status indicator 37 is a light which displays the status of apparatus 20. During charging of rechargeable battery 34, status indicator 37 is green. Status indicator 37 will be red (a warning) when the voltage of rechargeable battery 34 is low. In this instance apparatus 20 must be immediately plugged in to an AC outlet in order to keep operating. Status indicator 37 will also be red if a leak in bladder 24 is detected and maximum cuff pressure is not reached in 30 seconds. In this instance, and audio alarm is also sounded. Status indicator will also be red if a bladder overpressure is detected.

In an embodiment rechargeable battery 34 is a 3.7 volt Li-ion battery that powers all electrical components of apparatus 20. Rechargeable battery 34 can be connected to AC power via a battery charger/AC adapter while in use, thereby allowing uninterrupted prolonged service.

Figure 8:
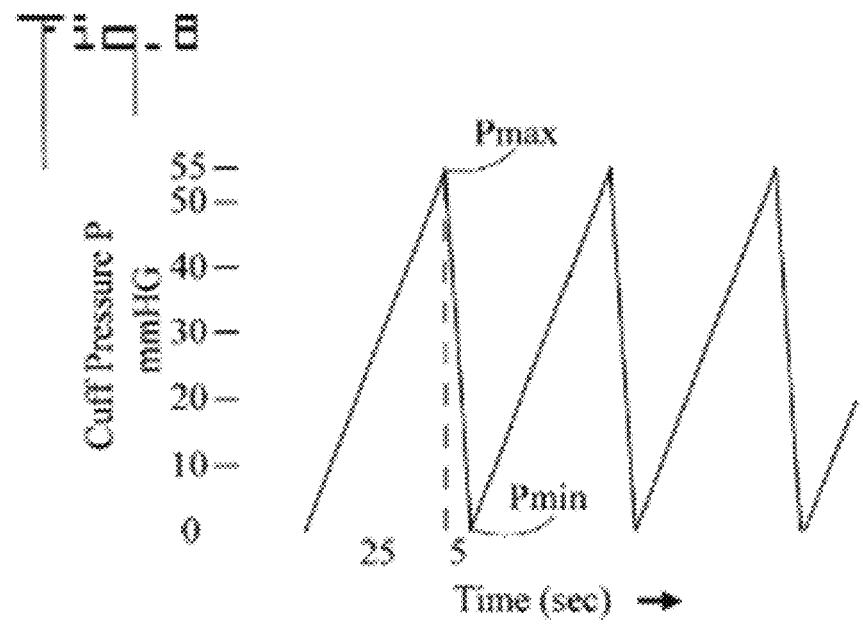
FIG. 8 is a third pressure application mode.
Figure 9:
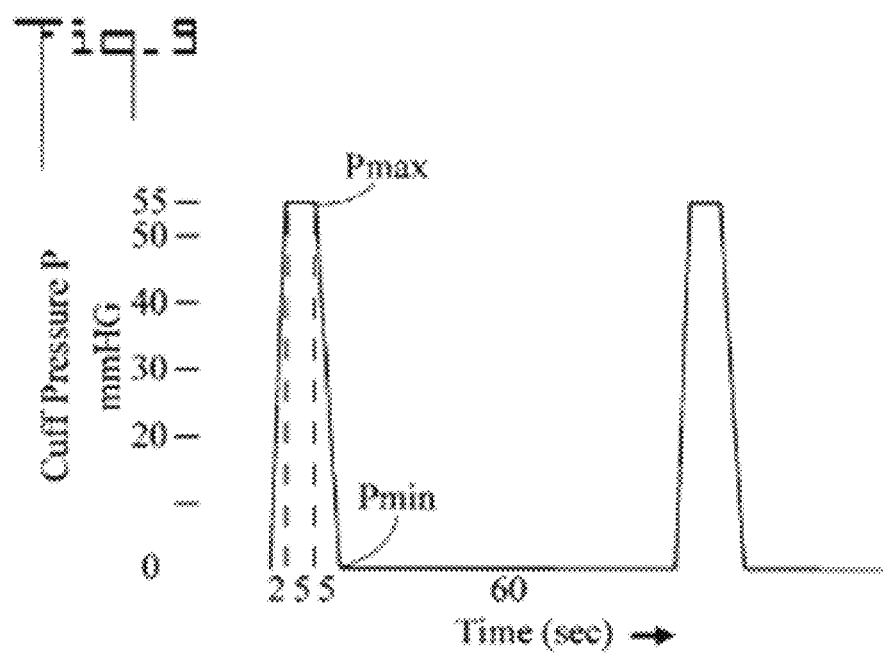
FIG. 9 is a fourth pressure application mode.

FIG. 6 is a first pressure application mode. As used herein, the term "pressure application mode" is the time variable value of cuff pressure P [typically measured in millimeters of mercury (mmHg), above ambient pressure)] as a function of time (typically measured in seconds). As can be seen from FIG. 6, cuff pressure P is plotted along the ordinate while time is plotted along the abscissa. When used, apparatus 20 will apply pressure to the limb 500 of the patient (refer to FIG. 1) in accordance with the selected pressure application mode. It is noted that FIG. 6 represents only one possible pressure application mode. Other pressure application modes are shown in FIGS. 7-9, however it may be appreciated that apparatus 20 can be programmed to implement any other desired. pressure application mode.

In the shown embodiment apparatus 20 applies cuff pressure P from 0 mmHg to 55 mmHg in 20 seconds. The cuff pressure P is held at 55 mmHg for 10 seconds, and then it takes 5 seconds for the bladder 24 to deflate and cuff pressure P to return to 0 mmHg, wherein the limb 500 relaxes without any pressure. Then in 60 seconds the cycle is repeated. This cyclic process continues while apparatus 20 is operating.

In this embodiment the maximum cuff pressure P is 55 mmHg. Existing devices have a maximum pressure of 50 mmHg. In the present apparatus 20 more pressure is applied around the limb 500. With more pressure around the calf more blood is moved. The more movement of blood will help prevent stagnate blood from pooling behind a blood valve.

FIG. 7 is a second pressure application mode. It is noted that each pressure application mode has a minimum cuff pressure Pmin and a maximum cuff pressure Pmax. For the four pressure application modes shown in FIG. 6-9, the minimum pressure Pmin is 0 mmHg and the maximum pressure Pmax is 55 mmHg. The pressure application mode of FIG. 7 shows a step pressure application mode in which cuff pressure P holds (remains constant) for a period of time at at least one intermediate cuff pressure P between the minimum cuff pressure Pmin and the maximum cuff pressure Pmax. In the shown embodiment, the step pressure application mode contains a plurality of 10 mmHg steps in which cuff pressure P is held at each step for a period of time before rising to the next step. Cuff pressure P is increased in 10 mmHg steps from 0 mmHg to 50 mmHg, and then in a last step is increased by 5 mmHg to 55 mmHg. That is, the minimum cuff pressure Pmin is 0 mmHg, the maximum bladder pressure Pmax is 55 mmHg, with intermediate pressures of 10 mmHg, 20 mmHg, 30 mmHg, 40 mmHg, and 50 mmHg. In other words, at least one of the plurality of pressure application modes is a step pressure application mode which includes a plurality of increasing pressure steps, followed by a dwell period at the maximum cuff pressure, followed by a plurality of decreasing pressure steps. As shown the step pressure application mode includes a plurality of 10 mmHg steps and one 5 mmHg step. It is also noted that the increasing pressure steps are performed over a step period (40 seconds) which is longer than the dwell period (10 seconds).

The step pressure application mode can benefit a patient who is non ambulatory, not moving, and lying down, wherein the blood flows at a slower rate. When a patient is ambulatory blood is moving at higher rate. Step technology allows for a slow periodic increase of pressure behind the calf. This slower increase allows blood to move over a longer period of time. This feature can be thought of like a heart beat but as the unit inflates the beat is getting stronger.

FIG. 8 is a third pressure application mode. In this pressure application mode a cycle of pressure application and removal is repeated at least twice per minute. Two pressure cycles a minute allows for a reduction of venous stasis as opposed to one cycle a minute. More blood is moved per unit of time. It is noted that in the shown embodiment, the maximum cuff pressure is 55 mmHg and the minimum cuff pressure is 0 mmHg.

FIG. 9 is a fourth pressure application mode. In this embodiment, pump 26 (refer to FIG. 5) is capable of raising cuff pressure P from 0 mmHg to 55 mmHg within two seconds. A full inflation rate of two seconds or less allows an evacuation of more blood Doppler tests have shown that rapid inflation clears out the valve cusps at a greater rate than with a slow inflation rate.

Figure 10:
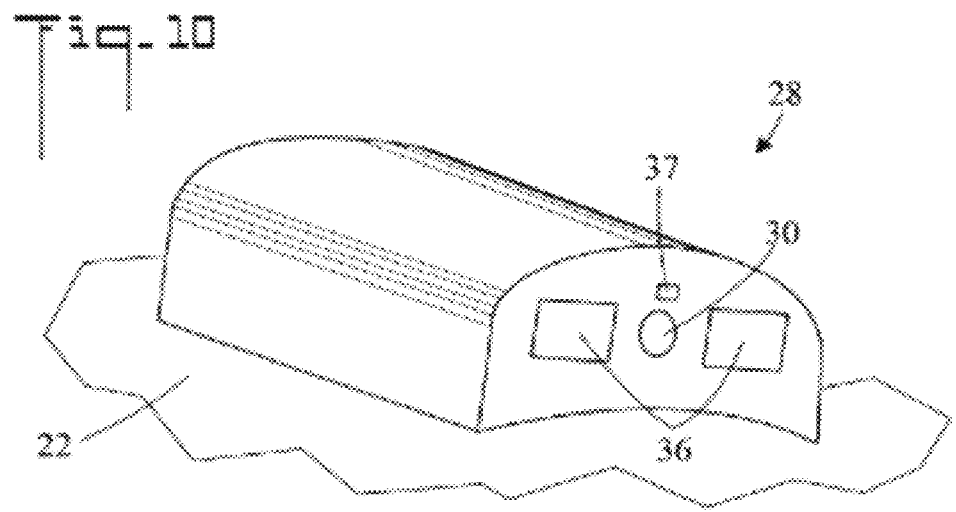
FIG. 10 is an enlarged fragmented perspective view of a housing.

FIG. 10 is an enlarged fragmented perspective view of housing 28. In the shown embodiment the following components are located in or on housing 28; pump 26, conduit 27, pressure application mode selector 30, rechargeable battery 34, display 36, status indicator 37, computer 50, pneumatic valve 52, and pressure transducer 54.

In the shown embodiment, pressure application mode selector 30 is a multi-purpose control (such as a button)

which also controls activation and deactivation of apparatus 20, and is physically disposed between two displays 36. Pressure application mode selector 30 is operable by the patient and has been specifically placed between the two displays 36 for patient selection of a desired pressure application mode, patient visibility of cuff pressure P, and patient visibility of apparatus status on status indicator 37.

Figure 11:
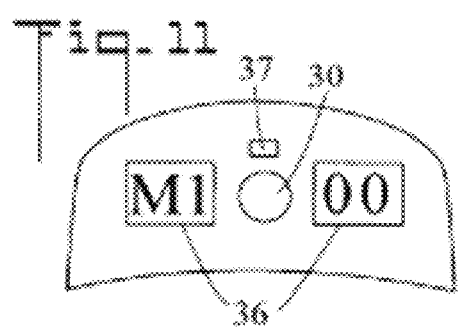
FIG. 11 is an enlarged view of a display.

FIG. 11-15 are enlarged views of display 36 at different times during the operation of apparatus 20. In FIG. 11 apparatus 20 has just been turned on by the patient using pressure selector 30. In the shown embodiment, apparatus 20 initially enters pressure application mode M1 as the default mode of operation. The left display 36 displays M1 and the right display shows real time cuff pressure P (which is initially 00 mmHg).

Figure 12:
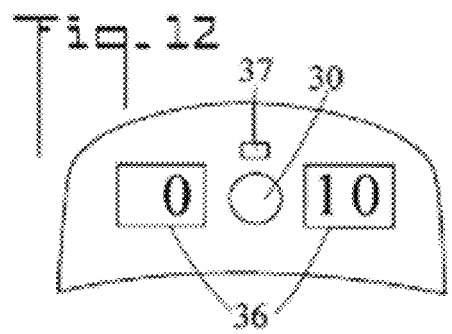
FIG. 12 is another enlarged view of the display.

FIG. 12 shows the state of apparatus 20 after a passage of time from FIG. 11 as cuff pressure P is being increased. The right display 36 shows a cuff pressure P of 10 mmHg. The left display shows the cumulative number of hours of apparatus 20 use. In this case the reading is 00 since this is the first time apparatus 20 has been used.

Figure 13:
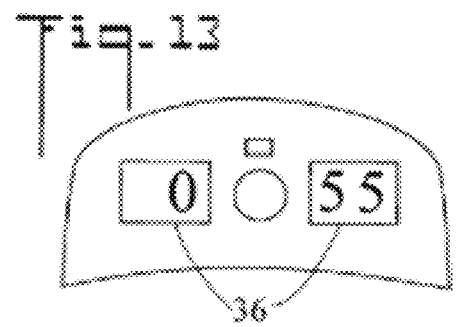
FIG. 13 is another enlarged view of the display.

FIG. 13 shows the state of apparatus 20 after a passage of time from FIG. 12 as cuff pressure P has continued to be increased. Right display 36 now shows that a maximum cuff pressure P of 55 mmHg has been achieved.

Figure 14:
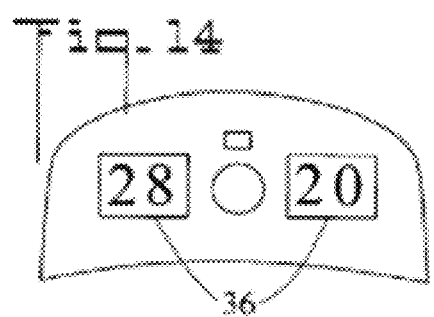
FIG. 14 is another enlarged view of the display.

FIG. 14 shows the state of apparatus 20 after 28 hours of cumulative use, which is shown on the left display 36. This cumulative time is saved when apparatus 20 is turned off, and will reappear and be the starting point when apparatus 20 is again turned on. Up to 99 hours of use can be logged. As shown, current cuff pressure P is 20 mmHg.

Figure 15:
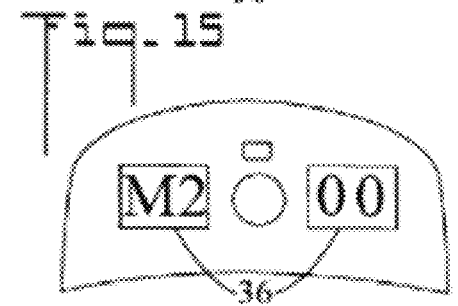
FIG. 15 is another enlarged view of the display.
Figure 16:
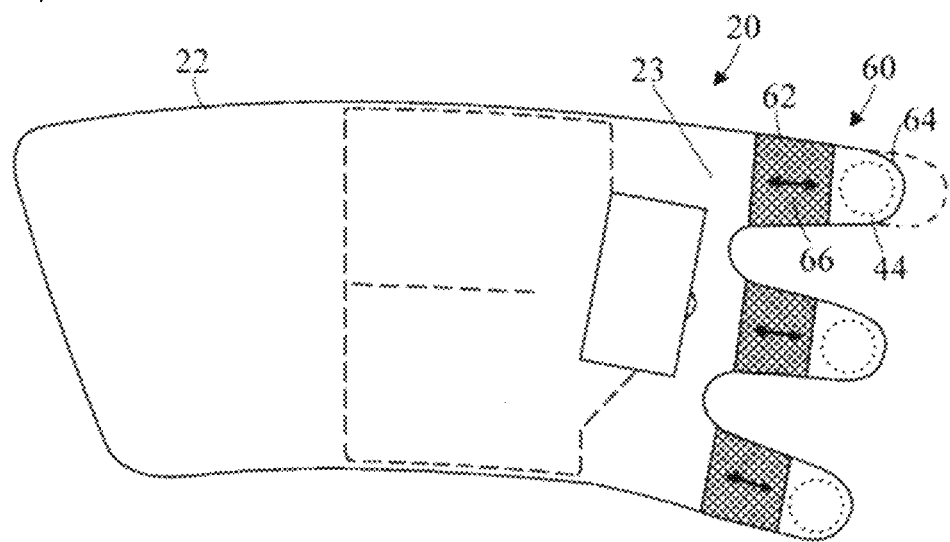
FIG. 16 is a view of a second embodiment of the apparatus.

FIG. 15 shows that apparatus 20 has changed to pressure application mode M2 by pressing the pressure application mode selector 30 once. The current cuff pressure P is 00 mmHg FIG. 16 is a view of a second embodiment of apparatus 20. Also referring to FIG. 4 and the associated discussion, cuff 22 includes a hook and loop fastener for securing cuff 22 to the limb 500 of the patient. The hook and loop fastener includes an outwardly projecting tab 60 which has a proximal end 62 and a distal end 64. One of hook and loop material (hook material 44 as shown) is disposed at distal end 64, and elastic material 66 disposed at proximal end 62. During the process of wrapping cuff 22 around the limb 500 of the patient, elastic material 66 is stretched as indicated by the dashed outline. Once the hook and loop fastener is connected, elastic material 66 resiliently applies pressure to the connection thereby better holding cuff 22 to the limb 500 of the patient. In the shown embodiment, cuff 22 has three tabs 60. It is further noted that cuff 22 has a body 23 which wraps around the limb of the patient, and that tab 60 outwardly projects from body 23. The elastic material 66 is not disposed at the distal end 64 of tab 60, but rather the elastic material 66 separates the body 23 of cuff 22 from the distal end 64 of tab 60.

Figure 17:
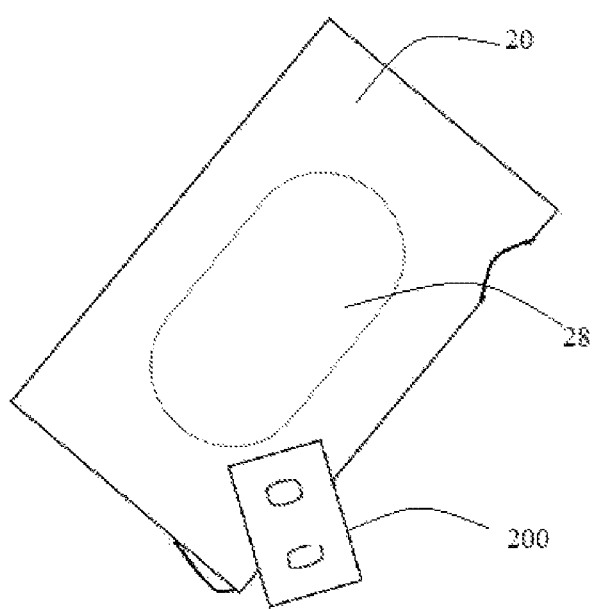
FIG. 17 is a perspective view that shows one of the embodiments of the present invention.
Figure 18:
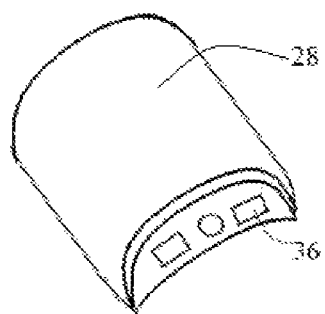
FIG. 18 is a perspective view that shows the display of the present invention.
Figure 19:
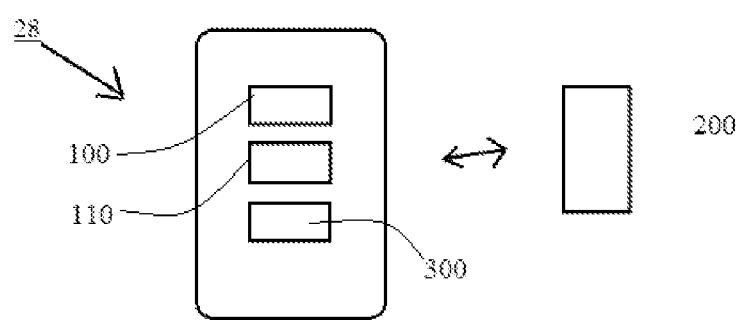
FIG. 19 is a box diagram that shows the housing (that shows microprocess, the transceiver, and the motion detector within the housing) and the remote of the present invention.
Figure 20:
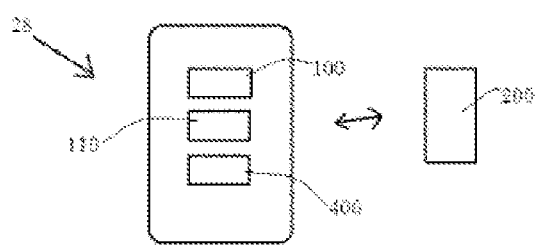
FIG. 20 is a box diagram that shows the housing (that shows microprocess, the transceiver, and the clap switch within the housing) and the remote of the present invention.

As seen in FIG. 17, in another embodiment of the present invention, the apparatus for applying periodic pressure to the limb of a patient to prevent deep vein thrombosis and pulmonary embolism, comprising: a cuff 22 having a bladder 24, the cuff 22 shaped and dimensioned to wrap around the limb 500 of the patient; a housing 28 that is attached to the cuff 22; a pump 26f or inflating the bladder 24 to a maximum cuff pressure, the maximum cuff pressure being 55 mmHg, the pump 26 is housed within the housing 28; a plurality of pressure application modes each of which control operation of the pump 26 and wherein each pressure application mode is progressively applied in a manner that will increase a patient's blood flow; a pressure application mode selector is disposed on the housing 28; a microprocessor 100 that is equipped with a program that controls the pump 26 and the plurality of pressure application modes, the microprocessor 100 is housed within the housing 28, the microprocessor 100 connects to a transceiver 110; and a remote 200 that connects via a radio frequency to the radio frequency transceiver 110 and that controls the microprocessor 100.

The remote 200 can be a smartphone, computer or tablet that connects to the microprocessor 100 via a radio frequency signal.

A further embodiment of the present invention comprises of a motion detector 300 that is connected to the microprocessor 100 and the motion detector 300 is housed within the housing 28 and wherein the microprocessor 100 can be turned on or off via a waving motion.

In still a further embodiment of the present invention, the invention comprises of a clap switch circuit 400 that is housed within the housing 28 and wherein the microprocessor 100 can be turned on or off via a clap.

In some embodiments of the present invention, the display 36 shows a cumulative number of hours of the apparatus use.

In terms of use, a method for applying periodic pressure to the limb 500 of a patient, includes: (refer to FIGS. 1-16)

(a) providing apparatus 20 for applying periodic pressure to the limb 500 of the patient, including;

a cuff 22 having a bladder 24, the cuff shaped and dimensioned to wrap around the limb 500 of the patient;

a pump 26 for inflating the bladder 24 to a cuff pressure P;

a plurality of pressure application modes which control operation of the pump 26;

a pressure application mode selector 30 disposed at the cuff 22, the pressure application mode selector 30 allowing a particular pressure application mode to be selected from the plurality of pressure application modes;

(b) wrapping the cuff 22 around the limb 500 of the patient;

(c) activating the apparatus 20;

(d) using the pressure application mode selector 30 to select a desired pressure application mode from the plurality of pressure application modes, wherein the pump 26 inflates the bladder 24 so as to apply cuff pressure P to the limb 500 of the patient in accordance with the desired pressure application mode.

The method further including:

(d) being performed by the patient.

The method further including:

in (a), each pressure application mode of the plurality of pressure application modes having a minimum cuff pressure Pmin and a maximum cuff pressure Pmax;

in (a), at least one of the pressure application modes of the plurality of pressure application modes being a step pressure application mode in which cuff pressure P holds for a period of time at at least one intermediate cuff pressure between the minimum cuff pressure Pmin and the maximum cuff pressure Pmax; and, in (d), selecting the step pressure application mode.

The method further including:

in (a), the pressure application mode selector 30 being a multi-purpose control which also controls activation and deactivation of apparatus 20; and, in (c), using the pressure application mode selector 30 to activate apparatus 20.

The method further including:

in (a), a display 36 disposed at the cuff 22; and, in (b), when the cuff 22 is wrapped around the limb 500 of the patient, the display 36 being viewable by the patient.

The method further including:

in (d), the display 36 displaying the cuff pressure P.

The method further including:

in (d), the display 36 displaying a cumulative number of hours of apparatus use.

The method further including:

in (a), the cuff 22 having an inside surface 40 which in (b) abuts the limb 500 of the patient;

in (a), a pressure switch 42 disposed at the inside surface 40 of the cuff 22, so that in (b) the pressure switch 42 closes, and if the pressure switch 42 is not closed, the pump 26 will not operate; and, in (b), ensuring that the cuff 22 is wrapped around the limb 500 of the patient such that the pressure switch 42 closes.

The embodiments of the apparatus and method of use described herein are exemplary and numerous modifications, combinations, variations, and rearrangements can be readily envisioned to achieve an equivalent result, all of which are intended to be embraced within the scope of the appended claims. Further, nothing in the above-provided discussions of the apparatus and method should be construed as limiting the invention to a particular embodiment or combination of embodiments. The scope of the invention is defined by the appended claims.

What is claimed is:

1. An apparatus for applying periodic pressure to a limb of a patient to prevent deep vein thrombosis and pulmonary embolism, comprising:
    a cuff having a bladder, the cuff shaped and dimensioned to wrap around the limb of the patient;
    a housing that is attached to the cuff a pump for inflating the bladder to a maximum cuff pressure, the maximum cuff pressure being 55 mmHg, the pump is housed within the housing, and wherein the pump raises the cuff pressure from 0 mmHg to 55 mmHg within two seconds;
    a plurality of pressure application modes each pressure application mode controls operation of the pump and wherein each pressure application mode is progressively applied in a manner that increases the patient's blood flow, wherein at least one of the pressure application modes of the plurality of pressure application modes has a cycle which is repeated at least twice per minute and the cycle has a maximum cuff pressure of 55 mmHg and has a minimum cuff pressure of 0 mmHg, wherein the at least one of the plurality of pressure application modes is a step pressure application mode which has a plurality of increasing pressure steps, followed by a dwell period after reaching the maximum cuff pressure, followed by a plurality of decreasing pressure steps, wherein the increasing pressure steps are conducted follows: first five 10 mmHg inflating steps and lastly one 5 mmHg inflating step, and wherein the increasing pressure steps are performed over a step period which is longer than the dwell period;
    a pressure application mode selector is disposed on the housing; a microprocessor that is equipped with a program that controls the pump and the plurality of pressure application modes, the microprocessor is housed within the housing, the microprocessor connects to a radio frequency transceiver that is a radiofrequency device;
    a remote that connects via a radio frequency to the radio frequency transceiver and that controls the microprocessor, and wherein the remote is a smartphone, computer or tablet that connects to the microprocessor via a radio frequency signal; and
    a motion detector that is connected to the microprocessor and the motion detector is housed within the housing and wherein the microprocessor is turned on or off via a waving motion.

2. An apparatus for applying periodic pressure to a limb of a patient to prevent deep vein thrombosis and pulmonary embolism, comprising:
    a cuff having a bladder, the cuff shaped and dimensioned to wrap around the limb of the patient;
    a housing that is attached to the cuff; a pump for inflating the bladder to a maximum cuff pressure, the maximum cuff pressure being 55 mmHg, the pump is housed within the housing, and wherein the pump raises the cuff pressure from 0 mmHg to 55 mmHg within two seconds;
    a plurality of pressure application modes each pressure application mode controls operation of the pump and wherein each pressure application mode is progressively applied in a manner that increases the patient's blood flow, wherein at least one of the pressure application modes of the plurality of pressure application modes has a cycle which is repeated at least twice per minute and the cycle has a maximum cuff pressure of 55 mmHg and has a minimum cuff pressure of 0 mmHg, wherein the at least one of the plurality of pressure application modes is a step pressure application mode which has a plurality of increasing pressure steps, followed by a dwell period after reaching the maximum cuff pressure, followed by a plurality of decreasing pressure steps, wherein the increasing pressure steps are conducted follows: first five 10 mmHg inflating steps and lastly one 5 mmHg inflating step, and wherein the increasing pressure steps are performed over a step period which is longer than the dwell period;
    a pressure application mode selector is disposed on the housing; a microprocessor that is equipped with a program that controls the pump and the plurality of pressure application modes, the microprocessor is housed within the housing, the microprocessor connects to a radio frequency transceiver that is a radiofrequency device;
    a remote that connects via a radio frequency to the radio frequency transceiver and that controls the microprocessor, and wherein the remote is a smartphone, computer or tablet that connects to the microprocessor via a radio frequency signal; and
    a clap switch circuit that is housed within the housing and wherein the microprocessor is turned on or off via a clap.

* * * * *